(12) United States Patent
Wang et al.

(10) Patent No.: US 6,451,904 B1
(45) Date of Patent: Sep. 17, 2002

(54) PREPARING STERILE ARTICLES FROM POLYMERS CONTAINING A STABILIZER BASED ON A POLY (OXYALKYLENE)

(75) Inventors: Qi Wang, Grand Island, NY (US); Sandor Nagy, Mason, OH (US)

(73) Assignee: Occidental Chemical Corporation, Dallas, TX (US)

( * ) Notice: Subject to any disclaimer, the term of this patent is extended or adjusted under 35 U.S.C. 154(b) by 0 days.

(21) Appl. No.: 09/973,566

(22) Filed: Oct. 9, 2001

Related U.S. Application Data

(62) Division of application No. 09/654,359, filed on Sep. 1, 2000, now Pat. No. 6,348,517.

(51) Int. Cl.[7] .................................................. C08J 3/00
(52) U.S. Cl. ...................... 524/569; 524/568; 524/567; 524/306; 568/8; 568/9; 568/10; 568/18; 568/37; 568/40; 568/579; 568/584; 568/59; 556/81; 556/85; 556/87
(58) Field of Search ................................ 524/306, 568, 524/567, 569; 525/46; 526/344, 344.3, 81; 568/8, 9, 10, 579, 18, 37, 40, 584, 590; 556/81, 85, 87; 49/245

(56) References Cited

U.S. PATENT DOCUMENTS

| | | | | |
|---|---|---|---|---|
| 3,976,616 A | * | 8/1976 | Combey et al. | 524/127 |
| 4,159,681 A | * | 7/1979 | Vandament | 108/57.33 |
| 4,478,961 A | * | 10/1984 | Tanaka et al. | 128/DIG. 22 |
| 4,569,953 A | * | 2/1986 | West et al. | 522/182 |
| 4,616,046 A | * | 10/1986 | Kornbaum et al. | 522/79 |
| 4,686,148 A | * | 8/1987 | Havens | 428/520 |
| 4,698,111 A | * | 10/1987 | Havens | 156/244.11 |
| 4,710,532 A | * | 12/1987 | Hull et al. | 524/310 |
| 5,011,660 A | * | 4/1991 | Arena | 422/21 |
| 5,077,331 A | * | 12/1991 | Fahey et al. | 524/317 |
| 5,155,184 A | * | 10/1992 | Laurent et al. | 526/348.4 |
| 5,352,721 A | * | 10/1994 | Takayanagi et al. | 524/183 |
| 5,830,937 A | * | 11/1998 | Shalov et al. | 428/502 |

OTHER PUBLICATIONS

Maruyama. Investigations of polyol derivatives. II. Effects of 2–ethylehexyl–2,3–dihydroxypropyl phthalate and its positional isomers as additives for polyvinyl chloride. (1983) Yukagaku 35(5), 262–265.*

* cited by examiner

*Primary Examiner*—James J. Seidleck
*Assistant Examiner*—Sanza L. McClendon
(74) *Attorney, Agent, or Firm*—Richard D. Fuerle

(57) ABSTRACT

Novel polymer stabilizers are disclosed. The novel stabilizers have the general formula $(R)_q Sn\text{-}(MR''\text{-}OCH_2\text{-}R'CH]_m\text{-}OT)_{4-q}$, $P\text{-}[(OCH_2\text{-}R'CH)_m OT]_3$,

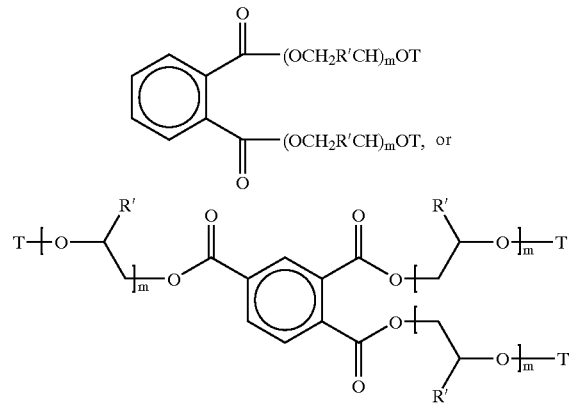

wherein M is O or S and R'' is $(CH_2)_p CO\text{-}$, $CO\text{-}(CH_3)_p$, or $CO(CH_2)_p\text{-}$. About 0.005 to about 65 phr of the stabilizer can be used in a polymer having a halogen-containing repeating unit, such as poly(vinyl chloride), to reduce yellowing of an article made from the polymer after the article has been exposed to gamma radiation.

20 Claims, No Drawings

PREPARING STERILE ARTICLES FROM POLYMERS CONTAINING A STABILIZER BASED ON A POLY (OXYALKYLENE)

This application is a division of application Ser. No. 09/654,359 filed Sep. 1, 2000, now U.S. Pat. No. 6,348,517, dated Feb. 19, 2002.

BACKGROUND OF THE INVENTION

This invention relates to the preparation of a sterile article made from a polymer having a halogen-containing repeatin unit, where the polymer contains a compound based on a poly(oxyalkylene) (POA). In particular, it relates to reducing the yellowing of an article made from poly vinyl chloride) (PVC) after exposure to gamma radiation by incorporating compounds based on poly(ethylene glycol) (PEG) and poly (propylene glycol) (PPG) into the PVC.

PVC is a versatile thermoplastic that is widely used for making medical articles and for food packaging due to its clarity, gloss, unique versatility, excellent functional performance, inertness to fluids, and relatively low cost. Medical devices and food packaging are usually sterilized before they are used. While ethylene oxide sterilization imposes little or no harmful effects on the physical properties of PVC, radiation sterilization, such as with gamma rays, can adversely affect the polymer, such as yellowing it, PEG, PEG dibenzoate, and PPG dibenzoate have been used as PVC plasticizers. They are primarily used as alternatives for phthlate plasticizer, such as dioctyl phthalate (DOP). The use of these materials may also improve other properties of PVC. (J. H. Lee, K. O. Kim, Y. M. Ju, J. Biomed. Mater. Res (Appl. Biomater)48, pages 328 to 334 (1999); W. D. Arendt, J. Lang, J. Vinyl & Additive Technology, 4(3), pages 184 to 188 (1998); W. D. Arendt, Plast. Eng. 35(9), pages 46 to 49 (1979); W. D. Arendt, Plast. Eng. 25, pages 410 to 412 (1979)).

SUMMARY OF THE INVENTION

We have discovered that POA-based compounds inhibit the yellowing of polymers having halogen-containing repeating units after exposure to sterilizing radiation. The stabilizers of this invention also improve the mechanical strength of PVC compounds and reduce or eliminate the need to use DOP.

Some of the stabilizers of this invention are novel compounds while others are commercially available.

DESCRIPTION OF THE PREFERRED EMBODIMENTS

The stabilizers of this invention have the general formula: TGOT', where each T is independently selected from R—, R—CO—, —P(R)$_2$, —P(OR)$_2$, —Si(R)$_3$, or —Si(OR)$_3$, T' is T or A[GOT]$_n$, each A is independently selected from LS—Sn(R)$_{3-q}$(SLJ)$_q$, L—O—Sn(R)$_{3-q}$(OLJ)$_q$, (CH$_2$)$_p$S—Sn(R)$_{3-q}$(S(CH$_2$)$_p$—J)$_q$, LCO$_2$Sn(R)$_{3-q}$(OLCO—J)$_q$, or LSn (Y)$_{3-q}$(LJ)$_q$ when n is 0, from CO, E, CO—E—CO, Si(R)$_2$, Si(OR)$_2$, (Si(R)$_2$G)$_r$, (CO—E—CO—G)$_r$, (CO—G)$_r$, or (E—G)$_r$ when n is 1, and from P, PO, and trimellitate when n is 2, Y is —SLJ, —SLOR, —OLJ, —OLR, —S(CH$_2$)$_p$—J, —S(CH$_2$)$_p$R, OLCO—J, or OLCOOR, G is (O—CH$_2$—R'CH)$_m$, J is O—(CH$_2$CR'HO)T, L is CO(CH$_2$)$_p$, each R is independently selected from R', aralkyl from C$_6$ to C$_{12}$, and alkaryl from C$_6$ to C$_{12}$, each R' is independently selected from hydrogen, alkyl from C$_1$ to C$_{12}$, and aryl from C$_6$ to C$_{12}$, E is alkylene from C$_1$ to C$_{12}$, aralkylene from C$_6$ to C$_{12}$, alkarylene from C$_6$ to C$_{12}$, arylene from C$_6$ to C$_{12}$, m is 1 to 20, n is 0 to 2, p is 0 to 10, q is 0 to 3, and r is 1 to 20. The ethers (T=R, T'=R) are preferred and R is preferably alkyl from C$_1$ to C$_8$ as those stabilizers are more effective, R' is preferably methyl or phenyl because they increase the lipophilicity of the stabilizers, resulting in better miscibility with the polymers. The A group is preferably CO—E—CO or (CO—E—CO—G)$_r$ because the lipophilicity of the materials can be tailored and these materials are easily prepared. The Y group is preferably —SLJ, —SLOR, —S(CH$_2$)$_p$—J, or —S(CH$_2$)$_p$R because they are more effective. Of the tin stabilizers, sulfer-containing tin stabilizers are preferred because they are better thermo stabilizers. Finally, m is preferably 2 to 5 as smaller values may be less effective and greater values may not be compatible with PVC, resulting in a hazy appearance, n is preferably 0 to 1 because these stabilizers can better inhibit the discoloration of the polymers, p is preferably 1 to 2 because these stabilizers are readily available, q is preferably 1 to 2 because those stabilizers are also better thermal stabilizers, and r is preferably 2 to 5 because they mix well with PVC. Preferably, all the T groups are identical as those stabilizers are easier to prepare.

The general formula includes PEG and PPG ethers: R—G—OR, PEG and PPG esters: R—CO—G—OCO—R, tin compounds: (R)$_q$Sn—(MR"—G—OT)$_{4-q}$, silicates: (R)$_3$—Si—G—Si(R)$_3$, phosphites: P—(GOT)$_3$, phosphates: OP—(GOT)$_3$, phthalates:

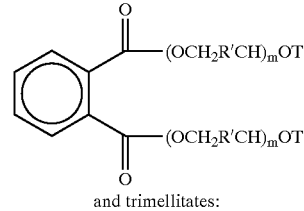

and trimellitates:

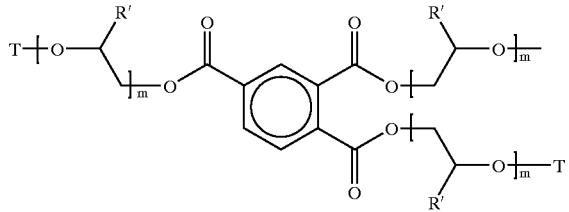

and trimellitates:

where M is O or S (and is preferably S) and R" is (CH$_2$)$_p$CO—, CO—(CH$_3$)$_p$CO—, —(CH$_2$)$_p$, or —O(CH$_2$)$_p$— (and is preferably (CH$_2$)PCO—).

Examples of PEG, PPG, and their ethers and esters include tri(propylene glycol), poly(propylene glycol), poly (propylene glycol)diglycidyl ether, dibutoxypropoxypropyl adipate, poly(propylene glycol di(2-ethylhexanoate), poly (propylene glycol) dibenzoate, di(propylene glycol) dibenzoate, poly(ethylene glycol) dibenzoate, and di(ethylene glycol) dibenzoate. Examples of tin compounds include dibutyltin bis(diethylene glycol monomethyl ether thioglycolate), dibutyltin bis(triethylene glycol monomethyl ether thioglycolate), dibutyltin bis(diethylene glycol monoethyl ether thioglycolate), dibutyltin bis(triethylene glycol monoethyl etherthioglycolate), dibutyltin bis(dipropylene glycol monoethyl etherthioglycolate), dibutyltin bis (tripropylene glycol monoethyl ether thioglycolate), bis(β-carbomethoxyethoxyethoxy)tin bis(isooctylthioglycoate), bis(β-carboethoxyethoxyethoxy)tin bis(isooctylthioglycoate), and bis(β-carboethoxyethoxyethoxyethoxy)tin bis(isooctylthioglycoate). Examples of silicates include poly(propylene glycol) bistrimethylsily ether, poly(propylene glycol) bistrimethoxysily ether, poly(ethylene glycol) bistrimethylsily ether, and poly(ethylene glycol) bistrimethoxysily ether. Examples of phosphites include tri(methoxyethoxyethyl) phosphite, tri(ethoxyethoxyethyl) phosphite, tri(methoxypropoxypropyl) phosphite, tri(ethoxypropoxypropyl) phosphite, tri(methoxyethoxyethoxyethyl) phosphite, tri(ethoxyethoxyethoxyethyl) phosphite, tri(methoxypropoxypropoxypropyl) phosphite, and tri(ethoxypropoxypropoxypropyl) phosphite. Examples of phosphates include tri(methoxypropoxypropyl) phosphate, tri(ethoxypropoxypropyl) phosphate, tri(methoxyethoxyethoxyethyl) phosphate, tri(ethoxyethoxyethoxyethyl) phosphate, tri(methoxypropoxypropoxypropyl) phosphate, and tri(ethoxypropoxypropoxypropyl) phosphate. Examples of phthalates include di(diethylene glycol monomethyl ether) phthalate, di(triethylene glycol monomethyl ether) phthalate, di(diethylene glycol monoethyl ether) phthalate, di(triethyiene glycol monoethyl ether) phthalate, di(dipropylene glycol monoethyl ether) phthalate, and di(tripropylene glycol monoethyl ether) phthalate. Examples of trimellitates include tri(diethylene glycol monomethyl ether) trimellitate, di(triethylene glycol monomethyl ether) trimellitate, di(diethylene glycol monoethyl ether) trimellitate, di(triethylene glycol monoethyl ether) trimellitate, di(dipropylene glycol monoethyl ether) trimellitate, and di(tripropylene glycol monoethyl ether) trimellitate. The preferred stabilizers are ethers and esters of PEG and PPG because many are commercially available.

Polyethylene glycol and polypropylene glycol ethers and esters that are not commercially available are easily made by, for example, condensing polyethylene glycol or polypropylene glycol with an alcohol (to make an ether) or with an acid chloride (to make an ester), as is well-known in the art. Of the above compounds, the PEG and PPG ethers, silyl ethers, and esters are well known. Phthalates such as dimethyl glycol phthalate, diethyl glycol phthalate, dibutyl glycol phthalate; di-2-(2-methoxyethoxy)ethyl phthalate; di-2-(2-ethoxyethoxy)ethyl phthalate; di-2-(2-butoxyethoxy)ethyl phthalate; di-2-(2-hexyloxyethoxy)ethyl phthalate; bis[2-[2-(2-ethoxyethoxy)ethoxy]ethyl] phthalate are also known. The known trimellitates include tris(2-methoxyethyl)trimellitates, and tris[2-(2-methoxyethoxy)ethyl]trimellitates; the known phosphorous compounds include tris(2-methoxyethyl)phosphite, tris2-(2-methoxyethoxy)ethyl]phosphite, tris(2-methoxyethyl) phosphate, tris[2-(2-methoxyethoxy)ethyl]phosphate, tris[2-[2-(2-methoxyethoxy)ethoxy]ethyl]phosphate. The tin compounds, some of the phosphites, phosphates, phthalates, and trimellitates are believed to be novel compounds. In particular, compounds having the general formula $(R)_q Sn$—$(MR''$—$OCH_2$—$R'CH]_m$—$OT)_{4-q}$, $P$—$[(OCH_2$—$R'CH)_m$—$OT]_3$,

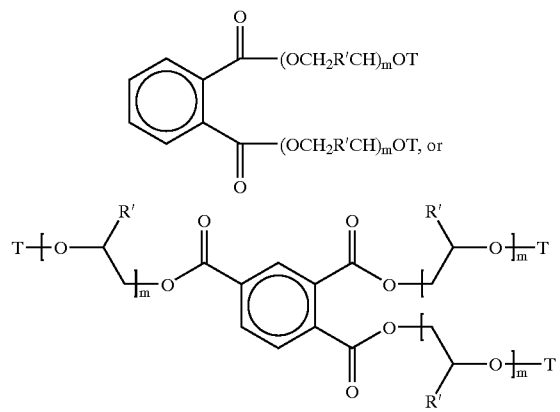

where each R' is independently selected from alkyl from $C_1$ to $C_{12}$, and aryl from $C_6$ to $C_{12}$, and R, M, T, m, and q are the same as hereinabove defined, are believed to be novel. They can be made by, for example, reacting $PCl_3$ with methyl monoethers of PEG or PPG. Stabilizers containing an $(CO$—$E$—$CO$—$G)_r$, $(CO$—$G)_r$, $(E$—$G)_r$, or $(Si(R)_2G)_r$ group are polymers made by reacting a difunctional acid, acid chloride, or anhydride, such as phosgene, adipic acid, malonic anhydride, or dichlorosilane with a PEG or a PPG.

The stabilizers of this invention are effective against the oxidation of haloginated polymers such as PVC, poly (vinylidene chloride), chlorinated polyethylene, and chlorinated polypropylene. The preferred polymer is PVC because PVC is more frequently used in medical applications where it is subjected to gamma radiation.

The polymer can be stabilized by the addition of about 0.005 to about 65 phr (parts by weight per 100 part by weight of the polymer) of the stabilizer to the polymer. Less stabilizer is less effective and more stabilizer offers little additional benefit; the preferred amount of stabilizer is about 0.2 to about 20 phr. The stabilizer can be added to the polymer in a variety of ways, such as by mixing the reactants at the beginning or during polymerization. The stabilizer is preferably added after at least 70 wt % of the monomer has polymerized. The stabilizer can be added as a solid or with a solvent as a slurry or a solution. Common organic solvents can be used, such as N-methylpyrrolidone, diglyme, acetamide, acetone, methanol, ethanol, isopropanol, dimethylsulfoxide, ordimethylformamide; water can also be used. Water miscible solvents, such as acetone, tetrahydrofuran, and methanol, are preferred for PVC. If the stabilizer is a solid, it is preferable to add the stabilizer in a solvent as that achieves a more uniform distribution of the stabilizer in the polymer. The stabilizer can also be added along with shortstop, or during the drying or compounding of the polymer. Various methods can be used for compounding, including milling, dry mixing, and extrusion. The stabilizers function as antioxidants to inhibit various forms of oxidation.

The following examples further illustrate this invention:

EXAMPLES 1 to 59

To a mixture of 150.00 g PVC (sold by Occidental Chemical Corporation as "Oxy 240" or by Oxy Vinyls as "OV 30"), 0.30 g stearic acid (used as a lubricant), 0.23 g of a zinc and calcium mixed salts of mixed fatty acids (used as a heat stabilizer; sold by Witco as "Mark 152 S"), 97.50 g dioctyl phthalate (used as a plasticizer to increase flexibility), minus the amount of stabilizer used, 15.00 g epoxidized soy bean oil (used as an HCl scavenger to reduce degradation; sold by Witco as "Drapex 6.8"), was added various amounts of different stabilizers. The mixture was thoroughly blended and hot milled at 300° F. (182° C.) for 5 minutes. The resulting PVC sheet was cut and pressed into a 4"×3"×¼" (10×8×0.6 cm) plaque at 330° F. (182° C.). The plaque was divided into two smaller pieces. One was saved for comparison and one was subjected to γ radiation at a dose of 50 kGy. The irradiated piece was again divided into two pieces and one of these pieces was oven aged at 50° C. for 48 hours. All of the samples were measured for yellowness index with a Macbeth 2020 Plus Color Eye Spectrometer, as described by the Hunter equations (see "The Measurement of Appearance" by Richard S. Hunter, John Wiley & Sons, New York, 1975). The following table gives the stabilizers used and the results.

| Example | Stabilizer | Amount (g) | Initial | After Radiation | After Aging |
|---|---|---|---|---|---|
| Control | none | none | 16.3 | 43.3 | 62.6 |
| 1 | Tri(propylene glycol) | 5.03 | 17.9 | 27.0 | 41.7 |
| 2 | " | 10.03 | 17.9 | 23.4 | 34.1 |
| 3 | " | 15.26 | 18.6 | 20.4 | 29.7 |
| 4 | Poly(propylene glycol) Mn = 425 | 3.44 | 18.5 | 32.2 | 50.9 |
| 5 | Poly(propylene glycol) Mn = 425 | 5.01 | 18.2 | 29.9 | 47.8 |
| 6 | Poly(propylene glycol) Mn = 425 | 7.61 | 16.3 | 25.7 | 42.1 |
| 7 | Poly(propylene glycol) Mn = 425 | 10.08 | 21.7 | 26 | 40.2 |
| 8 | Poly(propylene glycol) Mn = 425 | 15.06 | 20.7 | 25.7 | 38.0 |
| Control | none | none | 16.8 | 48.3 | 73.3 |
| 9 | Poly(propylene glycol) Mn = 425 | 15.05 | 20.3 | 27.2 | 38.3 |
| 10 | Poly(propylene glycol) Mn = 425 | 29.91 | 41.8 | 45.5 | 49.3 |
| 11 | Poly(propylene glycol) Mn = 725 | 3.5 | 17.9 | 39.1 | 58.5 |
| 12 | Poly(propylene glycol) Mn = 725 | 15.15 | 25.4 | 35.9 | 51.7 |
| Control | none | none | 16.3 | 43.3 | 62.6 |
| 13 | Poly(propylene glycol)diglycidyl ether Mn = 380 | 5.03 | 19.3 | 34.7 | 50.8 |
| 14 | Poly(propylene glycol)diglycidyl ether Mn = 380 | 10.02 | 19.3 | 31.1 | 45.9 |
| 15 | Poly(propylene glycol)diglycidyl ether Mn = 380 | 15.02 | 19.4 | 27.8 | 42.0 |
| 16 | Poly(propylene glycol)diglycidyl ether Mn = 640 | 5.02 | 19.0 | 34.4 | 50.7 |
| 17 | Poly(propylene glycol)diglycidyl ether Mn = 640 | 10.01 | 19.8 | 30.5 | 44.2 |
| 18 | Poly(propylene glycol)diglycidyl ether Mn = 640 | 15.02 | 19.1 | 28.0 | 42.5 |
| Control | none | none | 19.3 | 55.7 | 75.4 |
| 19 | Dibutoxypropoxy-propyl adipate[1] | 10.02 | 20.0 | 43.3 | 61.9 |
| 20 | Dibutoxypropoxy-propyl adipate[1] | 20.00 | 24.5 | 38.1 | 54.5 |
| 21 | Dibutoxypropoxy-propyl adipate[1] | 30.01 | 21.3 | 36.2 | 50.9 |
| 22 | Dibutoxypropoxy-propyl adipate[1] | 40.02 | 28.2 | 40.7 | 55.2 |
| 23 | Dibutoxypropoxy-propyl adipate[1] | 50.03 | 23.6 | 37.0 | 50.3 |
| 24 | Dibutoxypropoxy-propyl adipate[1] | 60.03 | 51.5 | 64.3 | 75.9 |
| 25 | Dibutoxypropoxy-propyl adipate[1] | 60.03 | 38.6 | 49.8 | 62.2 |
| Control | none | none | 21.1 | 57.2 | 77.2 |
| 26 | Poly(propylene glycol0 di(2-ethylhexanoate) | 14.6 | 18.6 | 51.7 | 70.1 |
| Control | none | none | 16.8 | 48.3 | 73.3 |
| 27 | Poly(propylene glycol) dibenzoate Mn = 400 | 3.5 | 17.4 | 43.5 | 64.9 |
| 28 | Poly(propylene glycol) dibenzoate Mn = 400 | 15.77 | 18.3 | 37.9 | 56.0 |
| 29 | Poly(propylene glycol) dibenzoate Mn = 400 | 30.21 | 18.9 | 35.6 | 52.3 |
| Control | none | none | 19.1 | 55.4 | 79.9 |
| 30 | Poly(propylene glycol) dibenzoate[2] | 10.03 | 17.5 | 47.1 | 68.9 |
| 31 | Poly(propylene glycol) dibenzoate[2] | 20.00 | 18.3 | 43.0 | 63.2 |
| 32 | Poly(propylene glycol) dibenzoate[2] | 30.02 | 18.2 | 41.6 | 57.6 |
| 33 | Poly(propylene glycol) dibenzoate[2] | 40.03 | 18.5 | 37.8 | 55.7 |
| 34 | Poly(propylene glycol) dibenzoate[2] | 50.02 | 17.1 | 38.4 | 54.1 |
| 35 | Poly(propylene glycol) dibenzoate[2] | 60.04 | 16.1 | 35.8 | 52.4 |
| Control | none | none | 16.9 | 61.7 | 84.1 |
| 36 | Di(propylene glycol) dibenzoate | 20.23 | 16.0 | 46.7 | 65.9 |
| 37 | Di(propylene glycol) dibenzoate | 40.46 | 16.9 | 43.2 | 59.8 |
| 38 | Di(propylene glycol) dibenzoate | 60.05 | 16.1 | 41.6 | 54.8 |
| Control | none | none | 19.3 | 61.6 | 79.0 |
| 39 | Poly(ethylene glycol) dibenzoate | 15.00 | 20.0 | 38.9 | 52.2 |
| 40 | Poly(ethylene glycol) dibenzoate | 30.04 | 20.0 | 33.1 | 42.8 |
| 41 | Poly(ethylene glycol) dibenzoate | 60.02 | 19.2 | 30.1 | 38.6 |
| Control | none | none | 19.1 | 55.4 | 79.9 |
| 42 | Mixture of PEG and PPG dibenzoates[3] | 10.05 | 17.9 | 49.8 | 68.8 |
| 43 | Mixture of PEG and PPG dibenzoates[3] | 20.03 | 16.0 | 43.6 | 60.7 |
| 44 | Mixture of PEG and PPG dibenzoates[3] | 30.03 | 17.0 | 41.2 | 55.4 |
| 45 | Mixture of PEG and PPG dibenzoates[3] | 40.02 | 16.7 | 37.9 | 51.2 |
| 46 | Mixture of PEG and PPG dibenzoates[3] | 50.06 | 16.7 | 37.6 | 49.6 |
| 47 | Mixture of PEG and PPG dibenzoates[3] | 60.04 | 16.7 | 36.2 | 47.4 |
| Control | none | none | 17.1 | 54.8 | 83.4 |
| 48 | Mixture of PEG and PPG dibenzoates[4] | 20.02 | 17.1 | 40.8 | 60.2 |
| 49 | Mixture of PEG and PPG dibenzoates[4] | 40 | 15.7 | 34.6 | 49.2 |
| 50 | Mixture of PEG and PPG dibenzoates[4] | 60.02 | 16.2 | 33.5 | 42.4 |
| 51 | Mixture of PEG and PPG dibenzoates[5] | 20.01 | 16.6 | 44.0 | 62.7 |
| 52 | Mixture of PEG and PPG dibenzoates[5] | 40.04 | 14.9 | 31.7 | 52.2 |
| 53 | Mixture of PEG and PPG dibenzoates[5] | 60.24 | 15.4 | 33.7 | 44.8 |
| 54 | Mixture of PEG and PPG dibenzoates[6] | 20.09 | 16.4 | 44.7 | 58.9 |
| 55 | Mixture of PEG and PPG dibenzoates[6] | 40.08 | 15.8 | 39.2 | 49.0 |
| 56 | Mixture of PEG and PPG dibenzoates[6] | 60.05 | 13.8 | 34.1 | 41.6 |

-continued

| | | Yellowness | | |
|---|---|---|---|---|
| Example | Stabilizer | Amount (g) | Initial | After Radiation | After Aging |
| 57 | Mixture of PEG and PPG dibenzoates[7] | 20.02 | 17.0 | 45.2 | 59.4 |
| 58 | Mixture of PEG and PPG dibenzoates[7] | 40.02 | 16.6 | 37.5 | 48.1 |
| 59 | Mixture of PEG and PPG dibenzoates[7] | 60.08 | 16.8 | 35.5 | 44.3 |

[1]Sold by C. P. Hall Company as "Plasthall ®DBPA"
[2]Sold by Unitex Chemical as "Uniplex 400"
[3]Sold by Velsicol as "Benzoflex 2088"
[4]Sold by Velsicol as "Benzoflex 2870"
[5]Sold by Velsicol as "Benzoflex 2888"
[6]Sold by Velsicol as "Benzoflex 2160"
[7]Sold by Velsicol as "Benzoflex 2860"

As can be observed from the above table, after gamma radiation the polymers that contained a stabilizer had significantly less discoloration than the control samples. The table also shows that a mixture of PEG- and PPG-based materials was also effective for stabilizing the PVC color after radiation. This feature makes it possible to tailor a stabilizer for a specific application if certain physical properties of the PVC are desired.

We claim:

1. A compound having the general formula $(R)_q Sn\text{-}(MR''\text{-}OCH_2\text{-}R'CH]_m\text{-}OT)_{4-q}$, $P\text{-}[(OCH_2\text{-}R'CH)_m OT]_3$,

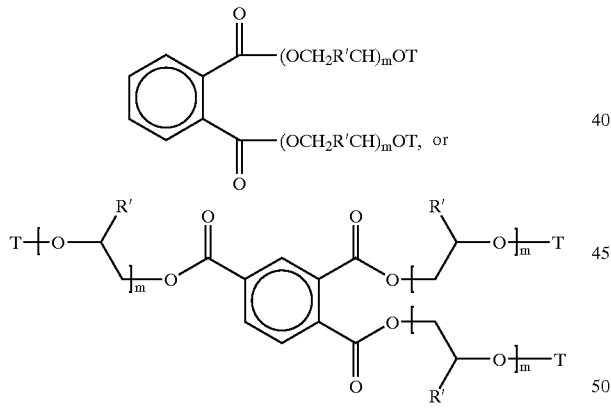

where M is O or S, each R is independently selected from R', aralkyl from $C_6$ to $C_{12}$, and alkaryl from $C_6$ to $C_{12}$, each R' is independtly selected from hydrogen, alkyl from $C_1$ to $C_{12}$, and aryl from $C_6$ to $C_{12}$, R" is $(CH_2)_p CO\text{-}, (CH_3)_p CO\text{-}, \text{-}(CH_2)_p$, or $CO(CH_2)_p\text{-}$, each T is independently selected from R-, R-CO-, -P(R)$_2$, -P(OR)$_2$, -Si(R)$_3$, or -Si)OR)$_3$, m is 1 to 20, p is 10 to 10, and q is 0 to 3.

2. A compound according to claim 1 having the formula $(R)_q Sn\text{-}(MR''\text{-}OCH_2\text{-}R'CH]_m\text{-}OT)_{4-q}$, where M is sulfur.

3. A compound according to claim 1 having the formula $P\text{-}[(OCH_2\text{-}R'CH)_m OT]_3$.

4. A compound according to claim 1 having th formula

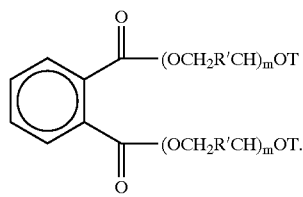

5. A compound according to claim 1 having the formula

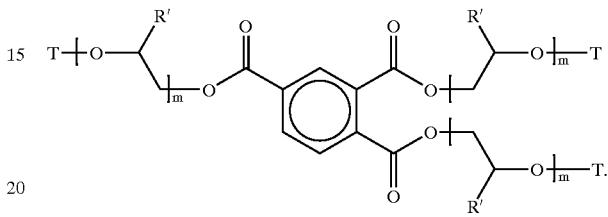

6. A compound according to claim 1 wherein R is alkyl from $C_1$ to $C_8$.
7. A compound according to claim 1 wherein R' is methyl or phenyl.
8. A compound according to claim 1 wherein R" is $(CH_2)_p CO\text{-}$.
9. A compound according to claim 1 wherein T is R.
10. A compound according to claim 1 T is alkyl from $C_1$ to $C_8$.
11. A compound according to claim 1 wherein m is 2 to 5, p is 1 to 2, and q is 1 to 2.
12. A compound according to claim 1 wherein all T groups are identical.
13. A compound according to claim 1 in a mixture with a polymer having a halogen-containing repeating unit, where the amount of said compound is about 0.005 to about 65 phr.
14. A polymer having a halogen-containing repeating unit, where said polymer is mixed with about 0.005 to 65 phr of a compound according to claim 1.
15. Poly(vinyl chloride) mixed with about 0.005 to about 65 phr of a compound according to claim 1.
16. A compound having the general formula $(R)_q Sn\text{-}(SR''\text{-}OCH_2\text{-}R'CH]_m\text{-}OT_{\_4-q}, P\text{-}[(OCH_2\text{-}R'CH)_m OT]_3$,

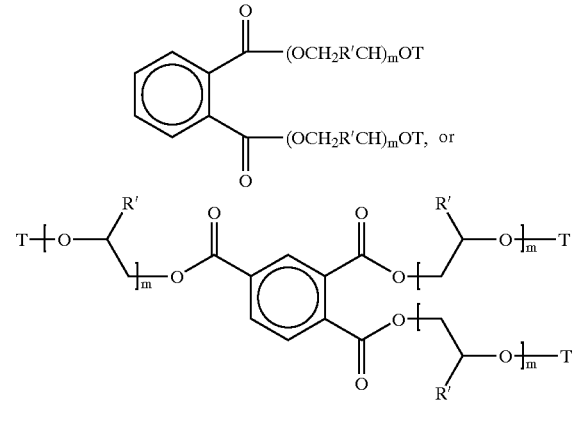

where each R is independently selected from hydrogen and alkyl from $C_1$ to $C_8$, each R' is independently selected from methyl or phenyl, R' is $(CH_2)_p CO\text{-}$, each T is independently selected from R, m is 2 to 5, p is 1 to 2, and q is 1 to 2.
17. A polymer having a halogen-containing repeating unit, where said polymer is mixed with about 0.2 to about 20 phr of a compound according to claim 16.

18. Poly(vinyl chloride) mixed with about 0.2 to about 20 phr of a compound according to claim 16.

19. A compound having the general formula $(R)_q Sn\text{-}(SR''\text{-}OCH_2\text{-}R'CH]_m\text{-}OT)_{4-q}$ or $P\text{-}[(OCH_2\text{-}R'CH)_m OT]_3$, where R is alkyl from $C_1$ to $C_8$, R' is methyl or phenyl, R" is $(CH_2)_p CO\text{-}$, T is R, m is 2 to 5, p is 1 to 2, and q is 1 to 2.

20. Poly(vinyl chloride) mixed with about 0.2 to about 20 phr of a compound according to claim 19.

* * * * *